(12) United States Patent
Sugino et al.

(10) Patent No.: US 6,413,447 B1
(45) Date of Patent: Jul. 2, 2002

(54) PHOTOCONDUCTING SILICON COMPLEXES, LIQUID CRYSTAL MATERIALS, COMPOSITION THEREOF, AND ELEMENTS USING SAME

(75) Inventors: Takushi Sugino; Yo Shimizu; Hirosato Monobe, all of Ikeda (JP)

(73) Assignees: Agency of Industrial Science and Technology; Ministry of International Trade and Industry, both of Tokyo (JP)

( * ) Notice: Subject to any disclaimer, the term of this patent is extended or adjusted under 35 U.S.C. 154(b) by 56 days.

(21) Appl. No.: 09/588,185

(22) Filed: Jun. 7, 2000

(30) Foreign Application Priority Data

Jun. 7, 1999 (JP) .......................... 11-158879

(51) Int. Cl.[7] .................. C09K 19/58; C09K 19/32; C08G 77/26; G03G 5/06; C07D 487/22

(52) U.S. Cl. .............. 252/299.3; 252/229.62; 430/58.2; 524/88; 528/43; 540/145

(58) Field of Search .................. 252/299.3, 299.62; 430/58.2, 78; 528/22, 43; 540/145; 524/88

(56) References Cited

U.S. PATENT DOCUMENTS 5,580,912 A * 12/1996 Hayashida et al. .......... 524/88

OTHER PUBLICATIONS

CAPALUS 1996:648557.*
CAPLUS 1988: 75084.*
CA 132: 7737 1999.*

* cited by examiner

Primary Examiner—Shean C. Wu

(74) *Attorney, Agent, or Firm*—Oblon, Spivak, McClelland, Maier & Neustadt, P.C.

(57) ABSTRACT

A substituted tetraphenylporphyrin silicon complex is represented by the general formula (I):

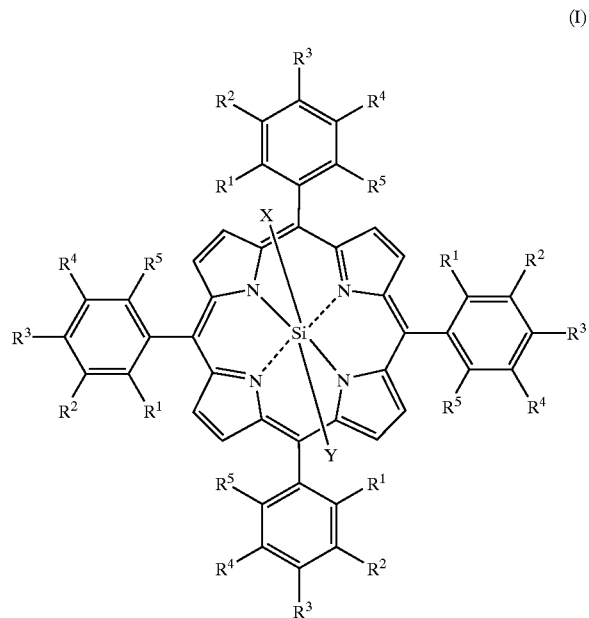

wherein $R^1$, $R^2$, $R^3$, $R^4$, and $R^5$ independently denote a hydrogen atom, an alkyl group, an alkoxy group, or a polyalkyleneoxy group, providing that the case in which $R^1$–$R^5$ invariably denote a hydrogen atom is excluded, and X and Y independently denote a hydroxyl group, an alkoxy group of C1–C3, or a halogen atom is disclosed. This invention embraces a substituted tetraphenylporphyrin silicon complex, polysiloxane, polysilane, liquid crystal material, photoconducting element, and photo-functional chaarge transfer material.

16 Claims, 1 Drawing Sheet

PHOTOCONDUCTING SILICON COMPLEXES, LIQUID CRYSTAL MATERIALS, COMPOSITION THEREOF, AND ELEMENTS USING SAME

BACKGROUND OF THE INVENTION

1. Field of the Invention

This invention relates to a substituted tetraphenylporphyrin silicon complex, polysiloxane, polysilane, a liquid crystal material, a photoconducting element, and a photofunctional charge-transfer material.

2. Description of the Prior Art

Heretofore, as respects the utility of a liquid crystal in the state intermediate state between solid and liquid in applications other than display element, some studies have been under way concerning the liquid crystal property and the photoconductivity of a discotic metal complex as a liquid crystal material of a new type altogether different in terms of molecular form from the conventional rodlike liquid crystal. The discotic liquid crystal as an electrically conductive material is characterized by manifesting a structure convenient for the transportation of holes or electrons (a columnar structure having disklike molecules stacked to produce a column) in the state of liquid crystal. Many materials have been known to allow satisfactory transportation of holes, whereas not many materials have been known to provide satisfactory transportation for electrons.

The present inventor has discovered for the first time that a novel porphyrin silicon complex exhibits a columnar lamellar liquid crystal phase and, on exposure to light on the surface of an ITO electrode, emits electron and constitutes a material for transporting electrons.

He has further discovered that the combination of this porphyrin silicon complex with a hole transporting agent promises development of a novel high-performance photofunction charge-transfer material (for example, an organic electroluminescent (EL) material).

SUMMARY OF THE INVENTION

An object of this invention, therefore, is to disclose an electron transferring material formed by a novel porphyrin silicon complex and teach a use thereof as a photofunctional charge-transfer material.

As a material conforming to this object, this invention contemplates a substituted tetraphenylporphyrin silicon complex represented by the following general formula (I):

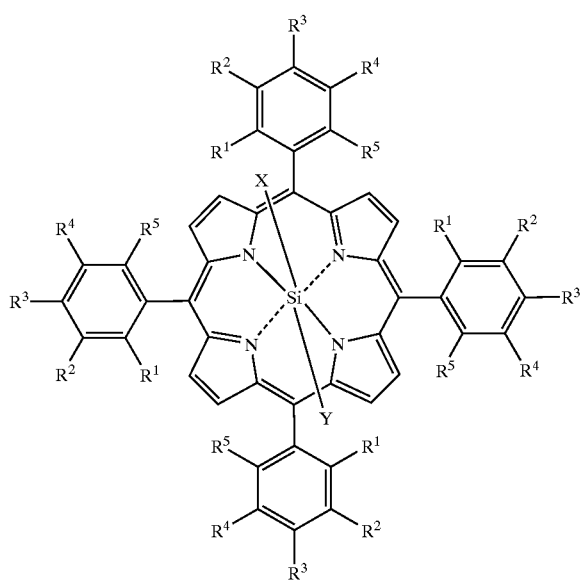

(I)

wherein $R^1$, $R^2$, $R^3$, $R^4$, and $R^5$ independently denote a hydrogen atom, an alkyl group, an alkoxy group, or a polyalkyleneoxygroup, providing that the case in which $R^1$–$R^5$ invariably denote a hydrogen atom is excluded, and X and Y independently denote a hydroxyl group, an alkoxy group of C1–C3, or a halogen atom.

The complex satisfies the general formula (1) by having $R^1$, $R^2$, $R^4$, and $R^5$ invariably denote a hydrogen atom, $R^3$ denote an alkyl group of 6–24 carbon atoms, and X and Y invariably denote an OH.

This invention further concerns a substituted tetraphenylporphyrin-containing polysiloxane containing a repeating unit represented by the general formula (II):

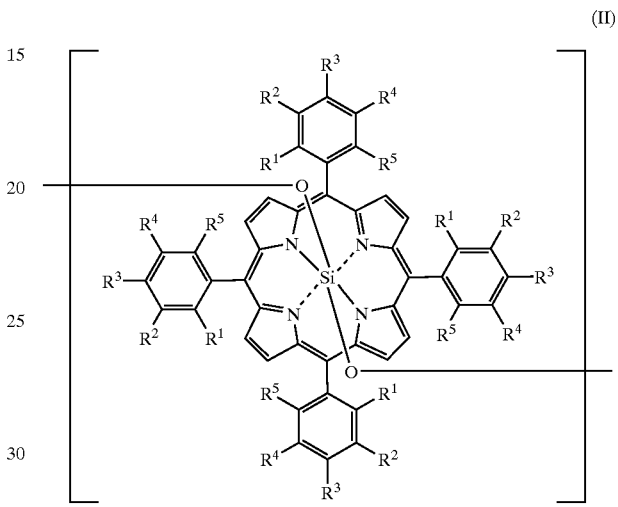

(II)

wherein $R^1$, $R^2$, $R^3$, $R^4$, and $R^5$ independently denote a hydrogen atom, an alkyl group, an alkoxy group, or a polyalkyleneoxygroup, providing that the case in which $R^1$–$R^5$ invariably denote a hydrogen atom is excluded and a siloxane type repeating unit as an arbitrary repeating unit.

This polysiloxane satisfies the general formula (II) by having $R^1$, $R^2$, $R^4$, and $R^5$ invariably denote a hydrogen atom and $R^3$ denote an alkyl group of not less than six carbon atoms.

This polysiloxane has a siloxane type repeating unit denoted by Si(—O—)$_4$, R—Si(—O—)$_3$, or R$_2$Si(—O—)$_2$ {wherein R denotes methyl, ethyl, n-propyl, or isopropyl}.

This invention further concerns a substituted tetraphenylporphyrin-containing polysilane comprising repeating units represented by the general formula (III):

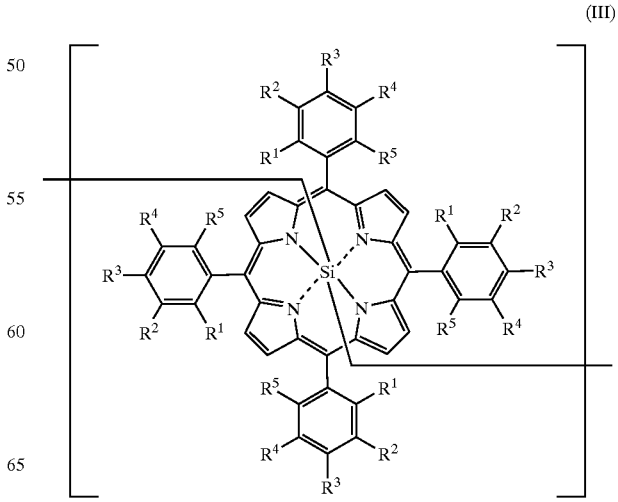

(III)

wherein $R^1$, $R^2$, $R^3$, $R^4$, and $R^5$ independently denote a hydrogen atom, an alkyl group, an alkoxy group, or a polyalkyleneoxy group, providing that the case in which $R^1$–$R^5$ invariably denote a hydrogen atom is excludes.

The polysilane satisfies the general formula (III) by having $R^1$, $R^2$, $R^4$, and $R^5$ invariably denote a hydrogen atom and $R^3$ denote an alkyl group of not less than six carbon atoms.

This invention further concerns a liquid crystal material comprising the substituted tetraphenylporphyrin silicon complex mentioned above and a liquid crystal material possessing a columnar lamellar phase.

This invention materializes a photoconducting element by forming on an electrode a film containing the substituted tetraphenylporphyrin silicon complex or the polysiloxane or the polysilane mentioned above.

The photoconducting element having ITO for the electrode is particularly important from the practical point of view.

Further, a photo-functional charge-transfer material is composed of the substituted tetraphenylporphryin silicon complex mentioned above and a hole transporting agent.

The photo-functional charge-transfer material is allowed to use a charge-transfer material for the purpose of serving as an organic EL element or a solid electrolyte.

DESCRIPTION OF THE PREFERRED EMBODIMENT

Figure 1:
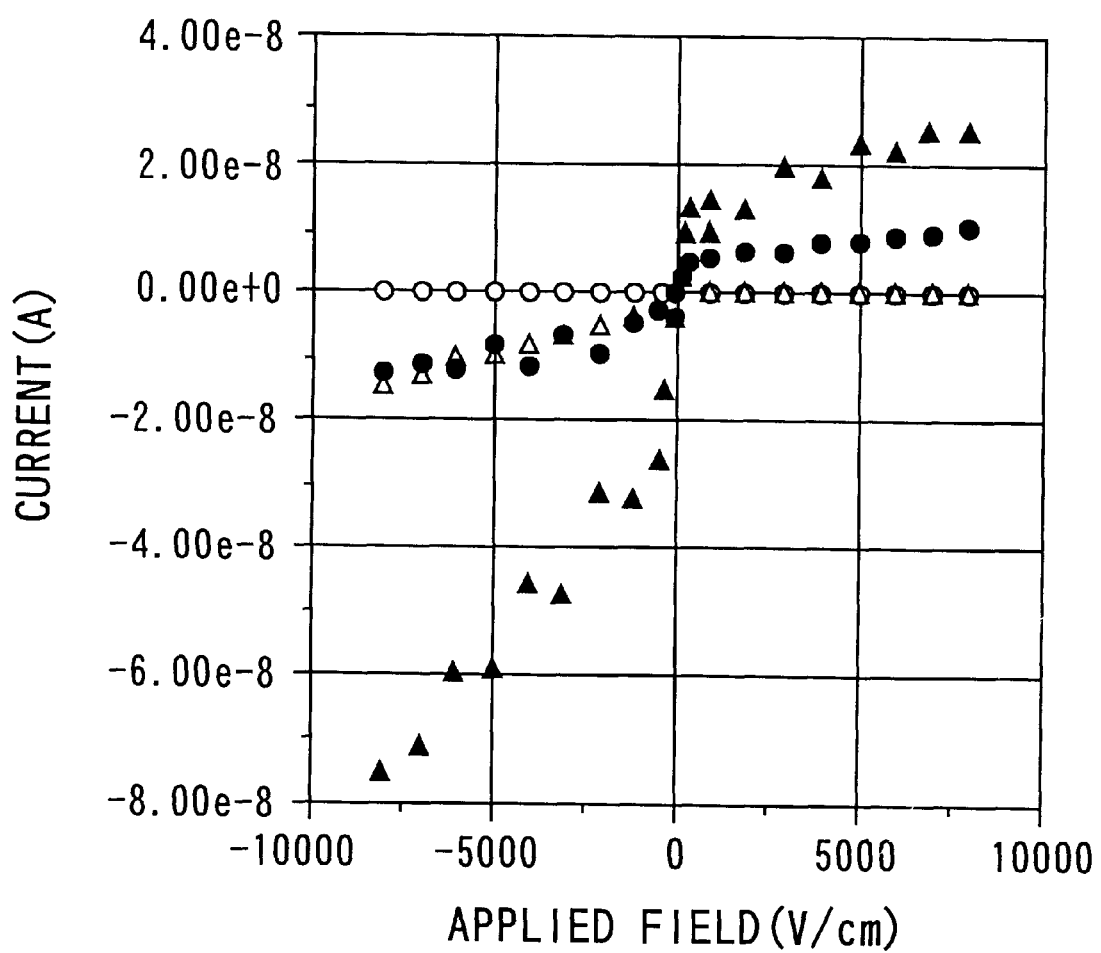
FIG. 1 is a graph showing the results of testing a cell having $C_{12}TPPSi(OH)_2$ sandwiched between two ITO electrodes [as represented by the formula, $ITO/C_{12}TPPSi(OH)_2/ITO$].

In this invention, as concrete examples of the alkyl group, alkyl groups of 6–24 carbon atoms, preferably 8–20 carbon atoms, including hexyl group, octyl group, decyl group, dodecyl group, tetradecyl group, hexadecyl group, octadecyl group, eicocyl group, dococyl group, and tetracocyl group may be cited.

As concrete examples of the alkoxy groups represented by $R^1$–$R^5$, alkoxy groups of 6–24 carbon atoms, preferably 8–20 carbon atoms, including hexyloxy group, octyloxy group, decyloxy group, dodecyloxy group, tetradecyloxy group, hexadecyloxy group, octadecyloxy group, eicocyloxy group, dococyloxy group, and tetracocyloxy group may be cited.

As concrete examples of the C1–C3 alkoxy groups represented by X or Y, methoxy group, ethoxy group, n-propoxy group, and isopropoxy group.

As concrete examples of the polyalkyleneoxy group, the groups represented by —O—{(CH$_2$CH$_2$)—O—}$_n$H (n denoting an integer in the range of 2–10), the groups represented by —O—{(CH(CH$_3$)CH$_2$)—O—)}$_n$H (n denoting an integer in the range of 2–10), and the groups represented by —O—{(CH$_2$CH(CH$_3$))—O—}$_n$H (n denoting an integer in the range of 2–10) may be cited.

The polysiloxane possessing a —Si—O—Si— structure is obtained by performing dehydration condensation where the groups represented by X and Y are hydroxyl groups or by performing dehydration condensation subsequent to hydrolysis where they are an alkoxy group or a halogen atom. The polysiloxane may be a homopolymer of a silicon complex (X=Y=OH) of the general formula or a copolymer with a siloxane type repeating unit.

As concrete examples of the siloxane type repeating unit, Si(—O—)$_4$, R—Si(—O—)$_3$, and R$_2$Si(—O—)$_2$ {R denoting methyl, ethyl, n-propyl, or isopropyl}. Preferably, Si{—O—}$_4$ and CH$_3$—Si(—O—)$_3$ may be cited.

The hole transporting agent is preferred to effect efficient injection of holes from an anode and to be capable of allowing the injected holes to be moved through a transportation layer at a high mobility.

As typical examples of the hole transporting agent, diamine derivative, hydrazone derivative, phthalocyaninederivative, and porphyrin derivative may be cited.

Where the groups represented by X and Y are halogen atoms, the polysilane possessing a —Si—Si— structure can be obtained by performing the condensation in the presence of organic metal compounds such as n-butyl lithium and phenyl lithium and metals such as lithium and sodium.

In this invention, the tetraphenylporphyrin as the ligant of a silicon complex is a known compound or can be easily synthesized from a known compound. The synthesis can be easily effected by the following method reported by Alder A. D., Longo F. R., Finarelli J. D., Goldmacher J., Assour J., Korsakoff, L., J. Org. Chem. 32 (1967) 467 with necessary modifications.

The general method for the production of the complex of this invention is represented by the following method of reaction process 1.

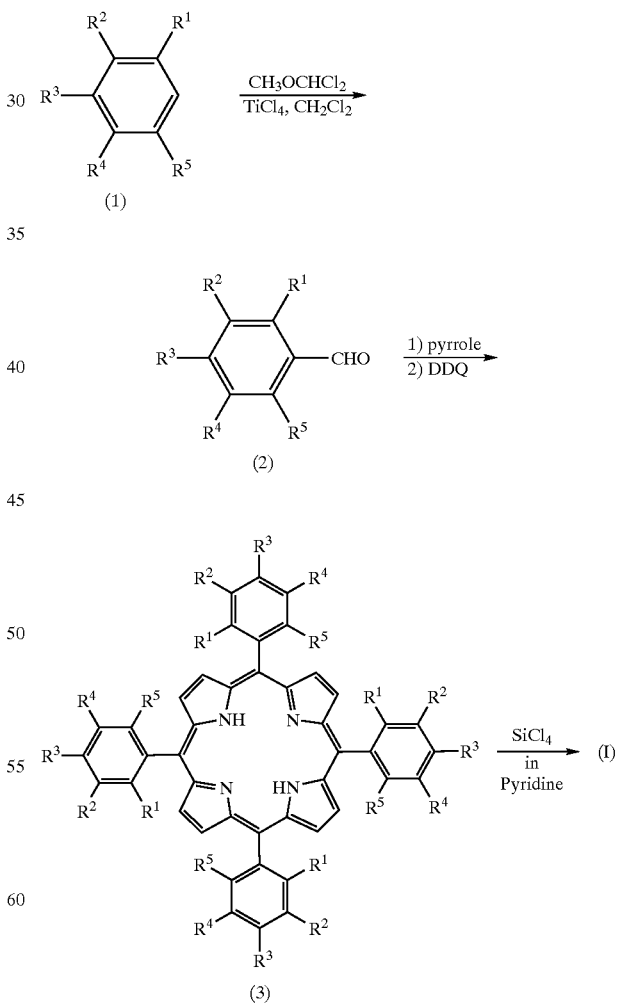

wherein $R^1$–$R^5$ have the same definitions as mentioned above).

In this invention, the substituted tetraphenylporphyrin (3) can be obtained by causing one mole of a benzene derivative (1) to react with 1–2 moles of 1,1-dichlorodimethyl ether and 1 mole to an excess of titanium tetrachloride in a solvent such as dichloromethane at a temperature in the range of 0° C.—room temperature for a period in the range of 30 minutes to five hours thereby obtaining an aldehyde (2), then causing 1 mole of the aldehyde (2) to react with 1–1.2 moles of pyrrole in a solvent such as propionic acid at a temperature in the range of room temperature and a temperature enough to reflux the solvent for one–ten hours, and subsequently allowing the reaction of the aldehyde with an equimole to an excess of DDQ to continue in a solvent such as benzene. The substituted tetraphenylporphyrin (3) thus obtained is enabled to produce the complex of the general formula (1) when it is allowed to react with $SiCl_4$ in pyridine, for example.

The purification of the obtained complex can be carried out by any of known purifying means such as column chromatography and recrystallization.

The silicon complex and the polysiloxane or polysilane containing this complex is inferred to assume the structure (columnar structure) having the substituted tetraphenylporphryrin in a superposed state. This structure is favorable for the transfer of holes or charges and is useful for a photoconductive elementelement or a photo-functional charge transfer material.

The complex of the general formula (1) which, for example, satisfies the formula by having $R^1$, $R^2$, $R^4$, and $R^5$ invariably denote a hydrogen atom and $R^3$ denote a dodecyl group ($C_{12}H_{25}$) and X and Y both denote a hydroxyl group exhibits a columnar lamellar $((Col)_L)$ structure which is the one liquid crystal phase in a temperature range of 84–211° C. The complex of this invention can be easily applied as a liquid crystal material between substrates coated with glass or ITO transparent conductive film without any decomposition. Thus, it allows various conducting materials to be easily manufactured by the conventional method. As concrete examples of the conducting material, photoconducting elements (sensitive materials and light receiving elements in electrophotography), photo-functional charge-transfer materials (organic EL elements and solid electrolytes), solar cells, electric fields sensors, magnetic fields sensors, ions sensors, heat sensors, and pH sensors, and liquid crystal display elements may be cited.

The compound of this invention evidently realizes photoconductive elements in the place of semiconductor layers which have already found utility as photoconducting material generally in sensitive materials for electrophotography and light receiving elements.

Now, the utility of the compound as a photo-functional charge transfer material in the organic EL element will be demonstrated below. This element as already known well is constructed by superposing a hole transporting agent layer and an electron transporting agent layer on a transparent electrode ITO and further superposing thereon a metal of low work function (such as Mg, Ag, or Al). The emission of light is induced by biasing the transparent electrode ITO toward the positive side of the metal of low work function thereby causing, the holes injected from the ITO into the hole transferring agent layer by bypassing the transparent electrode IT on the positive side and the electrons injected into the electron transferring agent layer from the electrode of low work function are recombined within the electron transferring agent layer or the hole transferring agent layer and consequently allowed to emit light. The cell thickness is about 100 nm. In this case, the compound of this invention is used for the electron transferring agent layer and diamine derivative, hydrazone derivative, phthalocyanine derivative, or porphryrin derivative enumerated above can be used for the hole transferring agent layer. A light emitting layer may be interposed between the hole transferring agent layer and the electron transferring agent layer. In this case, the electrons and the holes are mainly recombined in this light emitting layer. Also in this structure, the compound of this invention can be used in the same manner as mentioned above.

Further, since the compound of this invention can transport an alkali metal, the adoption of $LiCF_3SO_3$ or $LiClO_4$ as an electrolyte enables the compound of this invention to be used as a material for an alkali metal cell.

It is easily understood that the compound of this invention can be used as an organic material in the place of anthracene used in the light sensor of the type for measuring a change in electric resistance in consequence of exposure to light as reported in literature ("Hikari.Densi kinou-yuhkizairyou Handobukku (Handbook on Photo- and Electro-Functional Organic Materials)," compiled by Kazuyuki Horie Akio Taniguchi, Chapter 8 "Sensah Zairyoh (Sensor Materials)," pages 632–639, 1995, Asakura Shobo (ISBN 4-254-25236-6 C3058).

It is also evident that the compound can be used in the temperature sensor of the type utilizing an abrupt change in electric resistance in consequence of a phase transition reported in the literature mentioned above.

No particular difficulty is encountered in using the compound of this invention as an ion sensitive film in the ion sensor of the type of ion sensitive film reported in the literature mentioned above or as an ion selecting membrane on a gate electrode of an ISFET (ion sensitive FET).

The complex of this invention is endowed with such a temperature characteristic as realizes changes in the state of aggregation, i.e. liquid, liquid crystal, and solid, without undergoing decomposition, for example, and is useful as a liquid crystal in diverse applications.

The liquid crystal of this invention which is possessed of a columnar lamellar phase allows high density recording and permits production of highly satisfactory photoconducting elements and photo-functional charge transfer materials.

Now, this invention will be described more specifically below with reference to working examples. It should be noted, however, that this invention is not limited to these examples.

PRODUCTION EXAMPLE 1

Synthesis of 5,10,15,20-Tetrakis(4-n-dodecylphenyl)-21H,23H-porphyrin ($C_{12}TPPH_2$)

(1) Synthesis of p-n-Dodecylbenzaldehyde

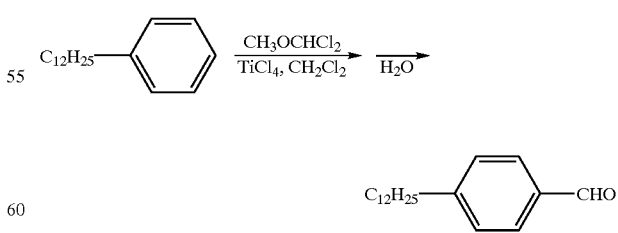

To 70 mL of dehydrated dichloromethane, 24.68 g (100 mmol) of n-dodecylbenzene was added and 36.82 g (189 mmol) of titanium tetrachloride was gradually added in drops. The reaction system kept below 10° C. in an ice bath and 13.16 9 (114 mmol) of 1,1-dichloromethl methy ether added in drops thereto were stirred together below 10° C. for 30 minutes and further stirred at a room temperature for 45 minutes. The resultant reaction mixture was added to 500 mL of ice water. It was extracted four times with 200 mL of dichloromethane and dried overnight on sodium sulfate. The solvent was removed by the use of an evaporator and purified by column chromatography (silica gel, benzene-:hexene =1:1). Consequently, 11.22 g (40.2 mmol) of a light yellow slightly viscous liquid was obtained. The yield was 40%.

$^1$H-NMR (500 MHz CDCl$_3$) 0.88 (t, J=7.0 Hz, 3H, —CH$_2$(CH$_2$)$_{10}$CH), 1.31–1.23 (m, 18H, —(CH$_2$)$_2$(CH$_2$)$_9$CH$_3$), 1.64 (quintet, J=7.4 Hz, 2H, —CH$_2$CH$_2$C$_{10}$H$_{21}$), 2.68 (t, J=7.8 Hz, 2H, —Ar—CH$_2$CH$_{11}$H$_{23}$), 7.33 (d, J=8.0 Hz, 2H, meta Ar), 7.79 (d, J=8.5 Hz, 2H, ortho Ar), 9.97 (s, 1H, —CHO).

(2) Synthesis of C$_{12}$TPPH$_2$

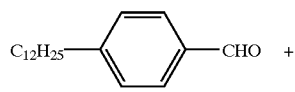

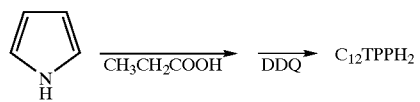

In an oil bath, 8.27 g (30.0 mmol) of the synthesized p-n-dodecylbenzaldehyde and 2.31 (34.4 mmol) of pyrrole and 91.5 mL of propionic acid placed therein were refluxed at 170° C. for 30 minutes. The resultant reaction mixture was left cooling to room temperature and left standing overnight in a refrigerator. The precipitate was separated by suction filtration and washed with acetone. This precipitate, 2.13 g in weight, was placed in chloroform (25 mL) and a solution of 0.38 g (1.7 mmol) of DDQ in 29 mL of benzene was added thereto and they were together refluxed at 70° C. for three hours. The reaction mixture consequently formed was deprived of the solvent by the use of an evaporator, purified by column chromatography (neutral alumina activity I, dichloromethane), further purified by column chromatography (neutral alumina activity II–III, benzene), and recrystallized from a 1/9 mixed solvent of benzene/acetone to obtain as a target product 2.10 g (1.6 mmol) of purple crystals of metallic gloss. The yield was 21%.

$^1$H-NMR (500 MHz CDCl$_3$) −2.75 (br, 2H, N—H), 0.88 (t, J=7.0 Hz, 12H, —(CH$_2$)$_{11}$CH$_3$), 1.31–1.58 (m, 72H, —(CH$_2$)$_2$(C$_9$H$_{18}$)CH$_3$), 1.90 (quintet, J=7.5 Hz, 8H, —CH$_2$C126C,OH$_{21}$), 2.93 (t, J=7.5 Hz, 8H, —Ar—CH$_2$C$_{11}$H$_{23}$), 7.53 (d, J=8.0 Hz, 8H, meta meso Ar), 8.10 (d, J=7.5 Hz, 8H, ortho Ar), 8.85 (s, 8H, pyrrole-H).

UV-vis(benzene) λmax (εmax, dm$^3$ mol$^{-1}$ cm$^{-1}$), 650 (5.8×10$^3$), 593 (6.4×10$^3$), 552 (1.2×10$^4$), 517(2.1×10$^4$), 421 (5.3×10$^5$) nm.

IR (Kbr): 3469.3 cm$^{-1}$ (N—H).

EXAMPLE 1

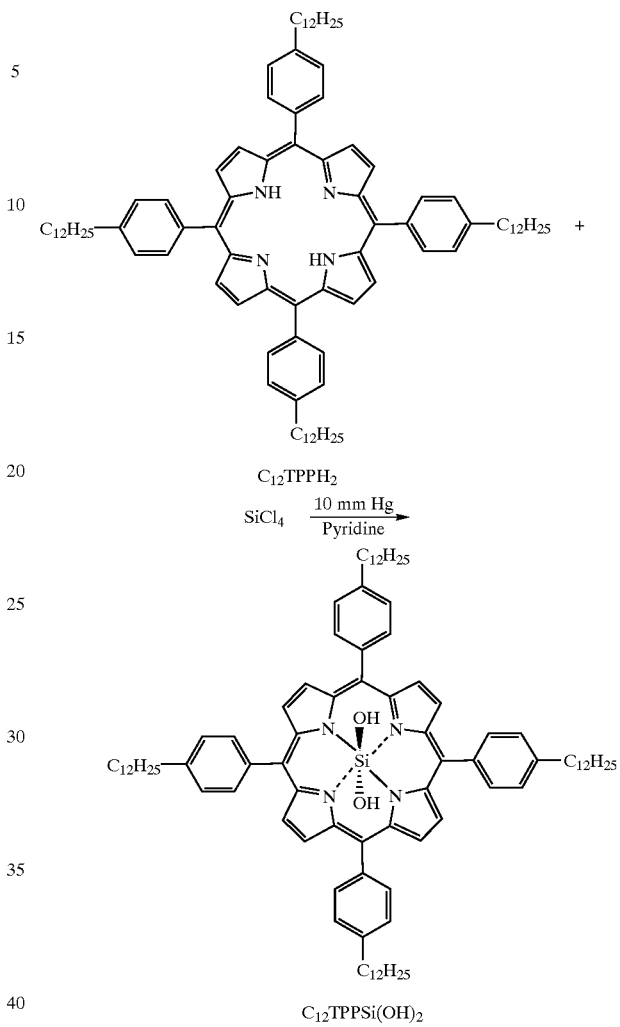

In a sealed glass tube, 0.78 g (0.6 mmol) of C$_{12}$TPPH$_2$, 0.76 g (0.6 mmol) of SiCl$_4$, and 30 ml of pyridine were left reacting under a reduced pressure of 10 mmHg at 190° C. for 48 hours to obtain C$_{12}$TPPSi(OH)$_2$ as expected in a yield of 48%.

The physical constants of the obtained C$_{12}$TPPSi(OH)$_2$ are shown below.

$^1$H-NMR (500 MHz, CDCl$_3$): −6.81 (s, 2H, OH), 0.88 (t, 12H, 4XCH), 1.29 (m, 56H, 4XCH$_3$(CH$_2$)$_7$), 1.52 (m, 8H, 4×X XC$_6$H$_4$CH$_2$CH$_2$CH$_2$), 1.87 (m, 8H, 4×X C$_6$H$_4$CH$_2$CH$_2$), 2.89 (t, 8H, 4×XC$_6$H$_4$CH), 7.50 (d, 8H, meta meso C$_6$H$_4$), 7.99 (d, 8H, ortho C$_6$H$_4$), 8.90 (s, 8H, β pyrrole-H).

$^{13}$C-NMR (CDCl$_3$, 126 MHz): δ14.1, 22.7, 29.4, 29.6, 29.7, 31.6, 31.9, 36.0, 11 7.5, 127.0, 131.6, 134.1, 137.8, 142.6, 143.4.

UV-vis(CH$_2$Cl$_2$) λmax, mol$^{-1}$, dm$^2$cm$^{-1}$): 593 (10100), 555 (20800), 423 (629400), 312 (20800) nm.

IR (Kbr): 3628 (O—H), 2923, 2583,1009, 852 (Si—O) cm$^{-1}$.

Elementary analysis (C$_{92}$H$_{126}$N$_4$O$_2$Si);
Calculated (%) C=81.97, H=9.42, N=4.16.
Found (%) C=81.67, H=9.72, N=4.15.

TEST EXAMPLE 1

It was revealed that the phase transition temperature of $C_{12}TPPSi(OH)_2$ was 84° C. and 211° C. for the transition from crystal to liquid crystal phase and the transition from liquid crystal phase to liquid(isotropic) phase, respectively. These phase transitions were confirmed by the texture observation with polarizing microscope and a differential scanning calorimetery. By the X-ray diffraction measurements, it has been demonstrated that the silicon complex exhibits a columnar lamellar phase in its liquid crystal phase.

TEST EXAMPLE 2

A cell ($ITO/C_{12}TPPSi(OH)_2/ITO$) (about 30 microns in film thickness) produced by sandwiching the $C_{12}TPPSi(OH)_2$ obtained in Example 1 between positive and negative electrodes both made of ITO was tested for properties of photoconductivity. The results are shown in FIG. 1. The horizontal axis of the graph is the scale of applied electric field and the vertical axis thereof the scale of dark current and intensity of photoelectric current. In FIG. 1, the mark, ○, denotes change in dark current in solid state (25° C.), the mark, ●, denotes change in dark current in liquid crystal state (100° C.), the mark, Δ, denotes change in photoelectric current in the solid state (25°), and the mark, ▼, denotes change in photoelectric current in liquid crystal (100° C.).

What is claimed is:

1. A substituted tetraphenylporphyrin silicon complex represented by the general formula (I):

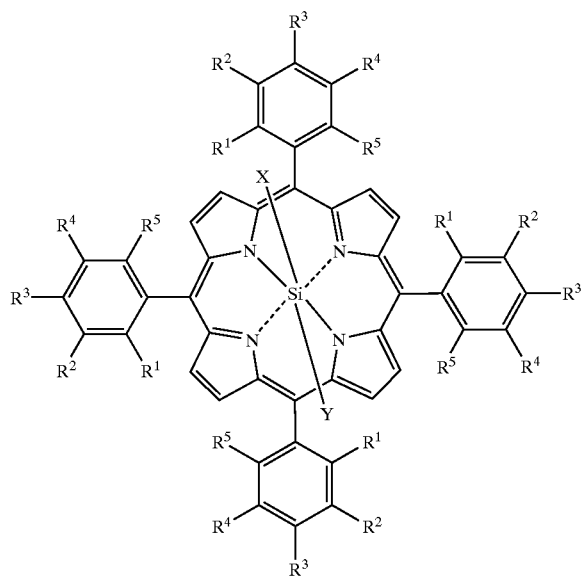

(I)

wherein $R^1$, $R^2$, $R^3$, $R^4$, and $R^5$ independently denote a hydrogen atom, an alkyl group, an alkoxy group, or a polyalkyleneoxy group, provided that the case in which $R^1$, $R^2$, $R^4$ and $R^5$ invariably denote a hydrogen atom and $R^3$ denotes an alkyl group of one carbon atom is excluded, and X and Y independently denote a hydroxyl group, an alkoxy group of C1–C3, or a halogen atom.

2. A complex according to claim 1, wherein $R^1$, $R^2$, $R^4$ and $R^5$ invariably denote a hydrogen atom, $R^3$ denotes an alkyl group of 6–24 carbon atoms, and X and Y both denote a hydroxyl group.

3. A tetraphenylporphyrin-containing polysiloxanes containing a repeating unit represented by the general formula (II):

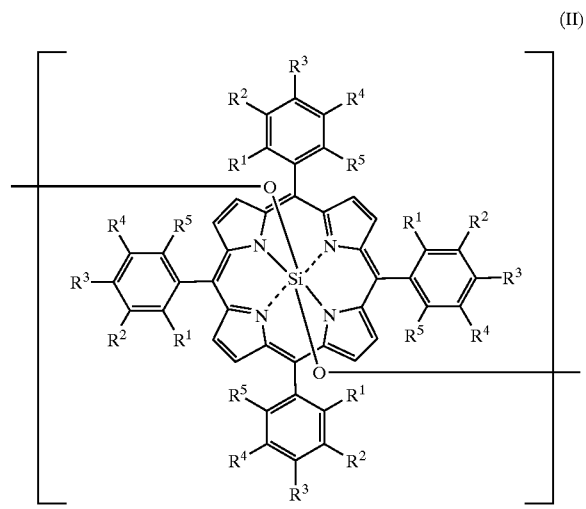

(II)

wherein $R^1$, $R^2$, $R^3$, $R^4$, and $R^5$ independently denote a hydrogen atom, an alkyl group, an alkoxy group, or a polyalkyleneoxy group, providing that the case in which $R^1$–$R^5$ invariably denote a hydrogen atom is excluded and a siloxane type repeating unit as an arbitrary repeating unit.

4. A polysiloxane according to claim 3, wherein $R^1$, $R^2$, $R^4$, and $R^5$ invariably denote a hodrogen atom and $R^3$ denotes an alkyl group of not less than 6 carbon atoms.

5. A polysiloxane according to claim 3, wherein said siloxane type repeating unit is $Si(-O-)_4$, $R-Si(-O-)_3$, or $R_2Si(-O-)_2$ {wherein R denotes methyl, ethyl, n-propyl, or isopropyl}.

6. A substituted tetraphenylporphyrin-containing polysilane comprising repeating units represented by the general formula (III):

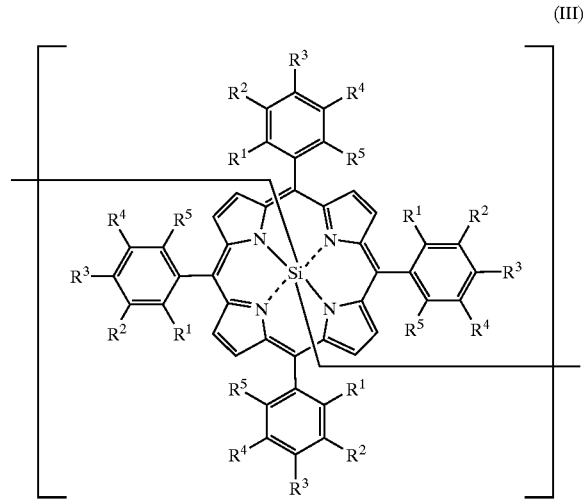

(III)

wherein $R^1$, $R^2$, $R^3$, $R^4$, and $R^5$ independently denote a hydrogen atom, an alkyl group, an alkoxy group, or a polyalkyleneoxy group, providing that the case in which $R^1$–$R^5$ invariably denote a hydrogen atom is excluded.

7. A polysilane according to claim 6, wherein $R^1$, $R^2$, $R^4$, and $R^5$ invariably denote a hydrogen atom and $R^3$ denotes an alkyl group of not less than six carbon atoms.

8. A liquid crystal material formed of the substituted tetraphenylporphyrin silicon complex set forth in claim 1 or claim 2.

9. A liquid crystal material according to claim 8, possessing a columnar lamellar phase.

10. A photoconducting element produced by forming on an electrode a film containing the substituted tetraphenylporphyrin silicon complex set forth in claim 1 or claim 2, the polysiloxane set forth in claim 4 or claim 5, or the polysilane set forth in claim 6 or claim 7.

11. A photoconducting element according to claim 10, wherein said electrode is an ITO.

12. A photo-functional charge transfer material containing the substituted tetraphenylporphyrin silicon complex set forth in claim 1 or claim 2 and a hole transporting agent.

13. A charge transfer material according to claim 12, wherein said photo-functional charge transfer material is an organic EL element or a solid electrolyte.

14. A method of making a substituted tetraphenylporphyrin silicon complex, the method comprising reacting a substituted tetraphenylporphyrin with $SiCl_4$ in pyridine; and producing the substituted tetraphenylporphyrin silicon complex of claim 1.

15. A method of making tetraphenylporphyrin-containing polysilioxane, the method comprising reacting a substituted tetraphenylporphyrin with $SiCl_4$ in pyridine to form a substituted tetraphenylporphyrin silicon complex; and producing the tetraphenylporphyrin-containing polysiloxane of claim 3 from the substituted tetraphenylporphyrin silicon complex.

16. A method of making substituted tetraphenylporphyrin-containing polysilane, the method comprising reacting a substituted tetraphenylporphyrin with $SiCl_4$ in pyridine to form a substituted tetraphenylporphyrin silicon complex; and producing the substituted tetraphenylporphyrin-containing polysilane of claim 6 from the substituted tetraphenylporphyrin silicon complex.

* * * * *

UNITED STATES PATENT AND TRADEMARK OFFICE
CERTIFICATE OF CORRECTION

PATENT NO.   : 6,413,447 B1
DATED        : July 2, 2002
INVENTOR(S)  : Sugino et al.

It is certified that error appears in the above-identified patent and that said Letters Patent is hereby corrected as shown below:

<u>Title page,</u>
Item [73], Assignee should read:

-- [73] Assignee: **Agency of Industrial Science and Technology,
             Ministry of International Trade and Industry,**
             Tokyo, Japan --

Signed and Sealed this

Eleventh Day of February, 2003

JAMES E. ROGAN
*Director of the United States Patent and Trademark Office*